(12) United States Patent
Plata

(10) Patent No.: US 10,926,104 B2
(45) Date of Patent: *Feb. 23, 2021

(54) INTRACAVITY BALLOON CATHETER

(71) Applicant: Myriad Medical LLC, Tampa, FL (US)

(72) Inventor: Fernando Plata, Atlanta, GA (US)

(73) Assignee: Myriad Medical LLC, Tampa, FL (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/139,976

(22) Filed: Sep. 24, 2018

(65) Prior Publication Data

US 2019/0022408 A1 Jan. 24, 2019

Related U.S. Application Data

(63) Continuation of application No. 14/991,464, filed on Jan. 8, 2016, now Pat. No. 10,179,249.

(Continued)

(51) Int. Cl.
*A61M 29/02* (2006.01)
*A61N 5/10* (2006.01)
*A61M 25/10* (2013.01)

(52) U.S. Cl.
CPC ........... *A61N 5/1002* (2013.01); *A61M 25/10* (2013.01); *A61N 5/10* (2013.01); *A61N 5/1014* (2013.01);
(Continued)

(58) Field of Classification Search
CPC .. A61M 25/10; A61M 25/0012; A61M 29/00; A61M 29/02; A61M 25/104;
(Continued)

(56) References Cited

U.S. PATENT DOCUMENTS 5,147,316 A 9/1992 Castillenti
5,335,669 A 8/1994 Tihon et al.
(Continued)

FOREIGN PATENT DOCUMENTS

CN 1408451 A 4/2003
CN 1787790 A 6/2006
(Continued)

OTHER PUBLICATIONS

European Office Action dated Apr. 10, 2018 for corresponding application No. EP15150382.6, 4 pages.
(Continued)

*Primary Examiner* — Vi X Nguyen
(74) *Attorney, Agent, or Firm* — Stephen J. Leahu; Alejandro J. Fernandez

(57) ABSTRACT

An intracavity balloon catheter may include a flexible catheter and a balloon provided on a distal end of the flexible catheter. The balloon may be inflatable with the introduction of fluid into the balloon from the flexible catheter. The balloon may be composed of a plurality of sections, including a center section and side sections. The inflated balloon may have shapes such as cylindrical, semi-cylindrical, or pillow shape. The intracavity balloon catheter may further include a securing device, such as a positioning ring, for securing the position of an inserted intracavity balloon catheter. This securing device may be composed of two, matable components with a passage extending through. The flexible catheter may be insertable into the passage. Tabs may be provided, either on one of the components or on a locking mechanism provided between the components, to prevent sliding of an inserted flexible catheter.

11 Claims, 6 Drawing Sheets

Related U.S. Application Data

(60) Provisional application No. 62/101,187, filed on Jan. 8, 2015.

(52) U.S. Cl.
CPC . *A61M 25/1002* (2013.01); *A61M 2025/1059* (2013.01); *A61M 2025/1086* (2013.01); *A61N 2005/1003* (2013.01); *A61N 2005/1097* (2013.01)

(58) Field of Classification Search
CPC ...... A61M 25/1002; A61M 2025/1059; A61M 2025/09008; A61B 2017/00557; A61N 5/10; A61N 5/1002; A61N 5/1014; A61N 5/0114
See application file for complete search history.

(56) References Cited

U.S. PATENT DOCUMENTS

| | | | |
|---|---|---|---|
| 5,355,087 | A | 10/1994 | Claiborne et al. |
| 5,476,095 | A | 12/1995 | Schnall et al. |
| 5,992,419 | A | 11/1999 | Sterzer et al. |
| 8,080,031 | B2 | 12/2011 | Isham |
| 8,241,317 | B2 | 8/2012 | Isham et al. |
| 8,454,648 | B1 * | 6/2013 | Isham ............... A61N 5/1049 128/DIG. 26 |
| 8,500,618 | B2 | 8/2013 | Isham |
| 8,500,771 | B2 | 8/2013 | Isham |
| 8,597,239 | B2 | 12/2013 | Gerrans et al. |
| 8,603,129 | B2 | 12/2013 | Isham |
| 8,679,147 | B2 | 3/2014 | Isham |
| 8,840,542 | B2 | 9/2014 | Plata |
| 9,126,035 | B2 | 9/2015 | Valoir |
| 9,227,084 | B2 | 1/2016 | Isham et al. |
| 9,381,334 | B2 | 7/2016 | Isham |
| 10,179,249 | B2 * | 1/2019 | Plata ................ A61N 5/10 |
| 2002/0010489 | A1 | 1/2002 | Grayzel et al. |
| 2003/0028097 | A1 | 2/2003 | D'Amico et al. |
| 2007/0010845 | A1 | 1/2007 | Gong |
| 2008/0021385 | A1 | 1/2008 | Barry et al. |
| 2008/0172080 | A1 | 7/2008 | Isham |
| 2008/0300619 | A1 | 12/2008 | Isham |
| 2009/0018446 | A1 | 1/2009 | Medan et al. |
| 2009/0221899 | A1 | 9/2009 | Isham |
| 2009/0276031 | A1 | 11/2009 | Kao |
| 2010/0145379 | A1 | 6/2010 | Isham |
| 2011/0044566 | A1 | 2/2011 | Fish et al. |
| 2012/0078177 | A1 | 3/2012 | Isham |
| 2014/0051968 | A1 | 2/2014 | Isham et al. |
| 2014/0261462 | A1 | 9/2014 | Visconti et al. |
| 2014/0357942 | A1 | 12/2014 | Plata |

FOREIGN PATENT DOCUMENTS

| | | |
|---|---|---|
| CN | 101164633 A | 4/2008 |
| CN | 202154945 U | 3/2012 |
| CN | 103209735 A | 7/2013 |
| CN | 203598366 U | 5/2014 |
| EP | 0720836 A2 | 7/1996 |
| EP | 0720836 A3 | 7/1996 |
| EP | 1060757 A1 | 12/2000 |
| EP | 3042687 A1 | 7/2016 |
| WO | WO9304727 A1 | 3/1993 |
| WO | WO94/12102 A1 | 6/1994 |
| WO | WO 97/21462 | 6/1997 |
| WO | WO 00/21584 | 4/2000 |
| WO | WO 02/07795 | 1/2002 |
| WO | WO 2007/065137 | 6/2007 |
| WO | WO 2007/098416 | 8/2007 |
| WO | WO 2009/152470 | 12/2009 |
| WO | 2013/066566 A1 | 5/2013 |
| WO | WO 2013/066566 A1 | 5/2013 |

OTHER PUBLICATIONS

International Search Report dated Sep. 16, 2011 for PCT/US2011/039957 filed Jun. 10, 2011.
Extended European Search Report for European Application No. 16140382.6, published Jul. 13, 2016, report dated May 31, 2016, 7 pages.
First Office Action of Applicant's Chinese Patent Application No. 201610243972.2 dated Nov. 26, 2019, 14 pages.
Office Action dated Oct. 12, 2017 in European Patent application No. 11726299.8, 4 pages.
Preliminary Search Report dated Jan. 27, 2015 (2 pages) of corresponding Chinese Patent Application No. 201180038859.6.
First Office Action dated Feb. 2, 2015 (7 pages) of corresponding Chinese Patent Application No. 201180038859.6.
International Preliminary Report on Patentability on PCT/US2011/039957 dated Dec. 10, 2012, 6 pages.
Written Opinion of the ISA of PCT/US2011/039957, 5 pages.
Second Office Action of Applicant's Chinese Patent Application No. 201610243972.2 dated Jul. 2, 2020, 16 pages.

* cited by examiner

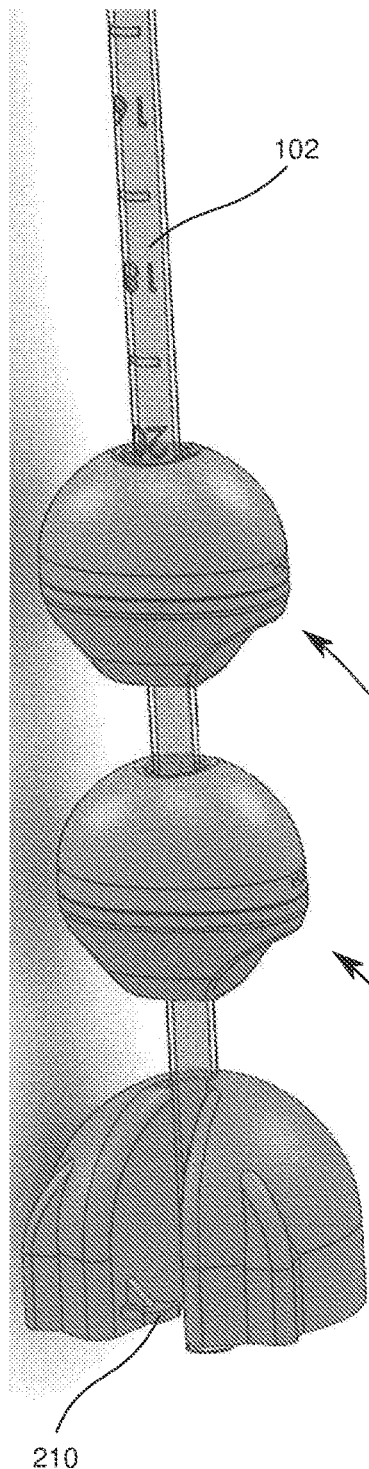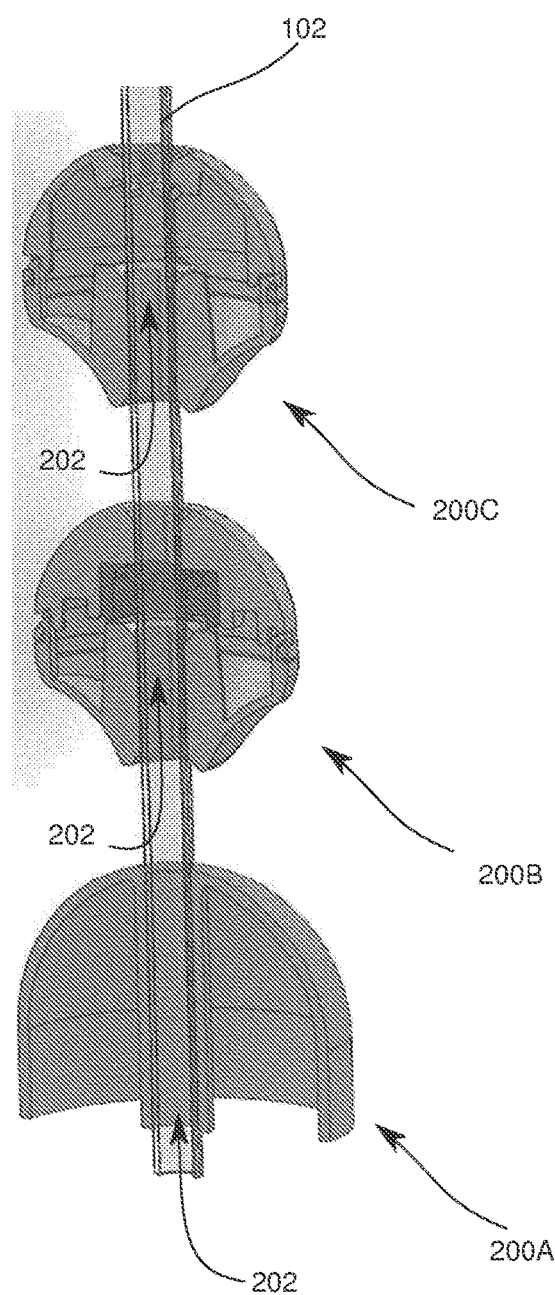
*FIG. 7*  *FIG. 8*

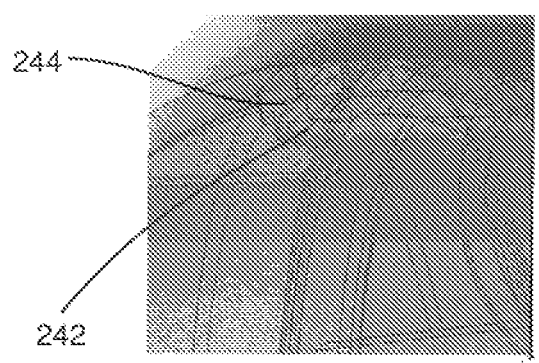
FIG. 9A
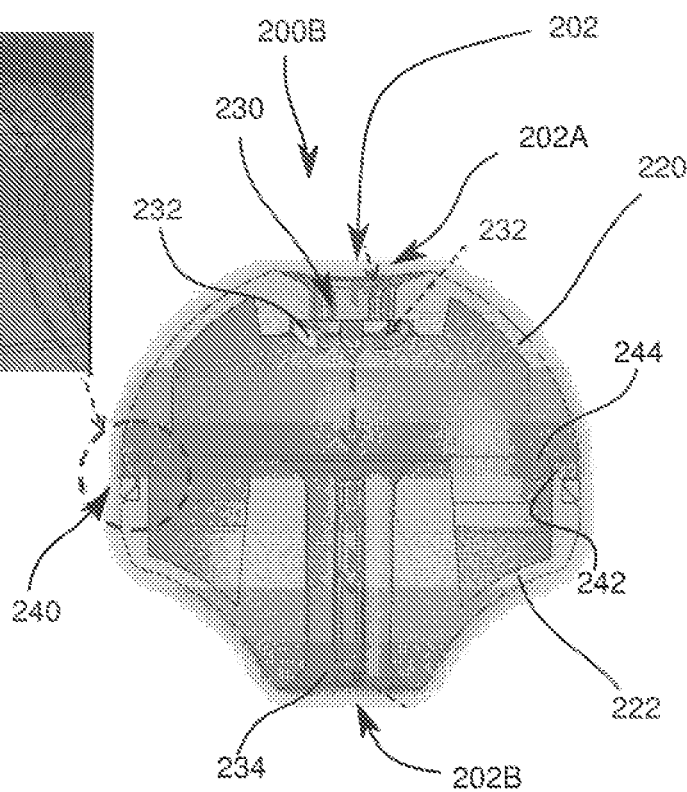
FIG. 9
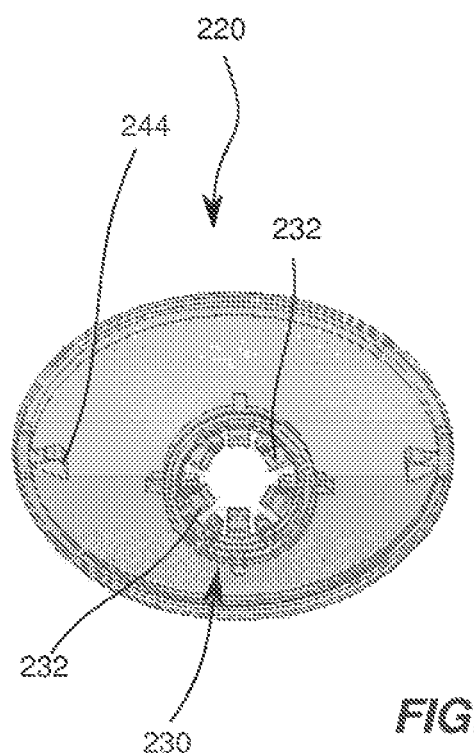
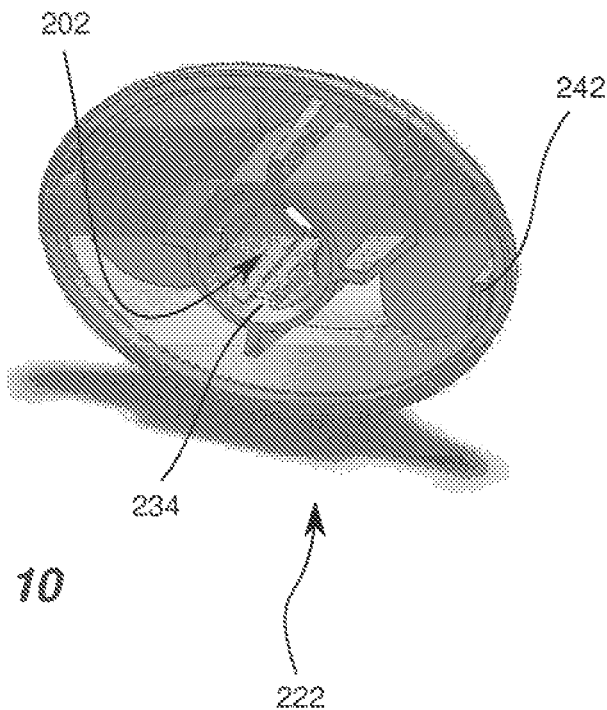
FIG. 10

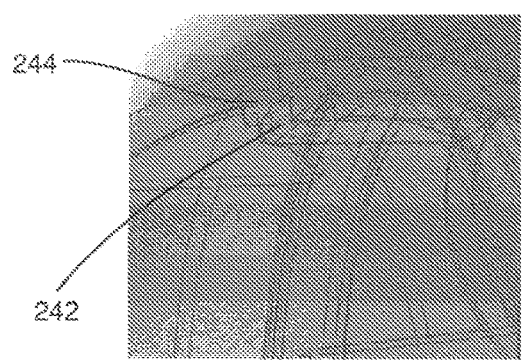
FIG. 11A
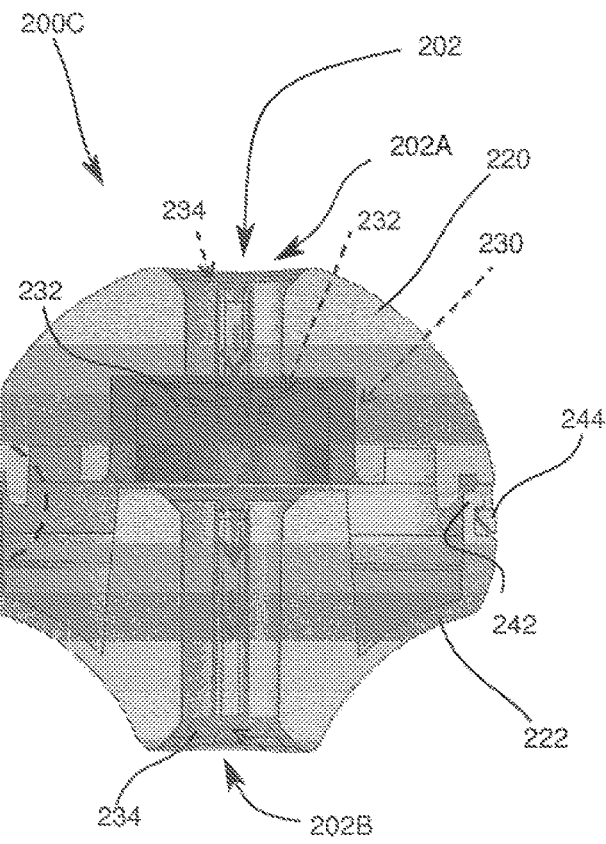
FIG. 11
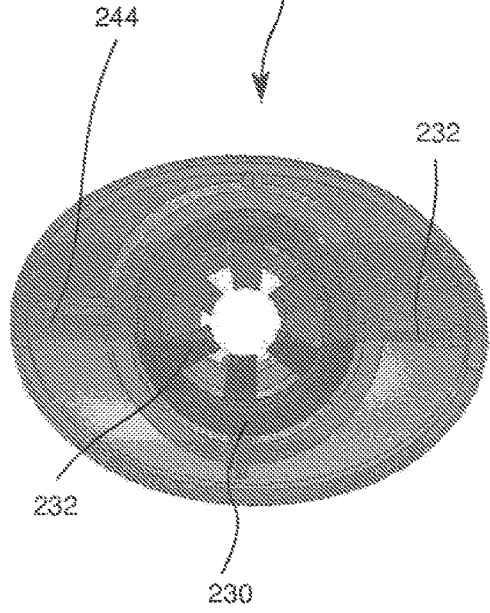
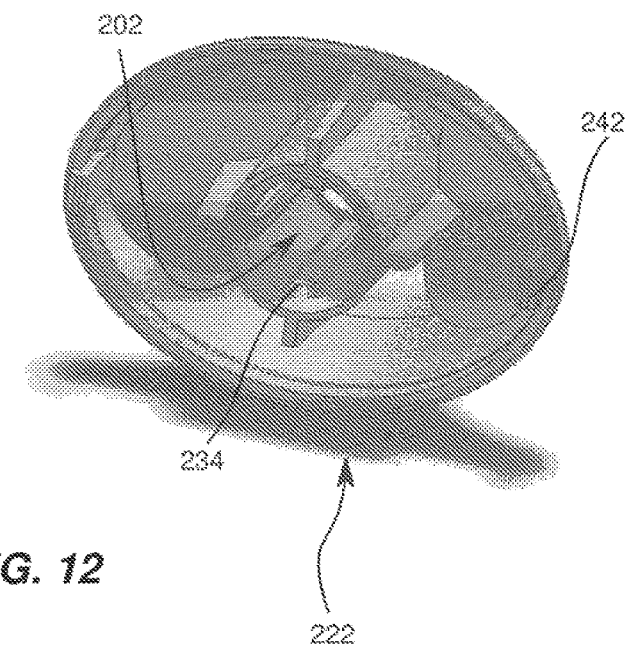
FIG. 12

INTRACAVITY BALLOON CATHETER

CROSS REFERENCE TO RELATED APPLICATIONS

This application claims priority to U.S. Provisional Patent Application No. 62/101,187 filed on Jan. 8, 2015, the entire contents of which are herein incorporated by reference.

FIELD OF THE DISCLOSURE

This disclosure relates generally to the diagnostic and therapeutic treatments of disease and, more particularly, an intracavity balloon catheter and method of use thereof to protect and stabilize the prostate region during staging process and radiation therapy treatment.

BACKGROUND

Radiation therapy treatment of soft tissue tumors in the prostate using radiation therapy treatment is complicated by the proximity of the prostate to radiation-sensitive tissues. Radiation therapy treatment of the prostate is further complicated by prostate movement during treatment.

Typically, the planning of radiation therapy for the treatment of prostate cancer involves the patient undergoing a CT-based simulation scan of the pelvis to determine the location of the prostate gland. In the simulation procedure, the patient is placed on CT and/or MM equipment that is similar to the radiation treatment equipment, except that it does not generate the high energy radiation beam. The simulation equipment is positioned to simulate the conditions experienced by the patient during delivery of the sequence of treatment beams prescribed by the treating oncologist. Normally, CT and/or MM images are acquired. These CT and/or MM images allow the oncologist to locate the position of the tumor and develop a radiation treatment plan using a tailored devoted radiation or proton therapy treatment plan. This treatment plan delineates the positions of the radiation equipment components for precise delivery of the radiation to a predetermined area.

During the subsequent treatment procedure, the patient is placed in the same position on the treatment equipment as in the simulation scans. Radiation-emitting devices are generally known and used for radiation therapy in the treatment of patients. During treatment, a radiation beam is delivered to the patient at the precise location as delineated by the physician during simulation. A further feature of radiation therapy involves portal images, which are commonly used to verify and record tumor location.

A large amount of attention has been directed to reducing the amount of pain and rectal bleeding resulting from radiation burns to, for instance, the rectal mucosa. One way physicians limit rectal bleeding is that they decrease the total radiation dose used to treat the patient's prostate cancer. However, this may lead to inadequate radiation treatment and a higher probability of local cancer recurrence. Another method physicians use to reduce rectal bleeding following radiotherapy is to immobilize the prostate with a balloon rectal catheter. The most common and oldest balloon catheter methods use a balloon that inflates in the rectum behind the prostate. This forces the posterior rectum away from the prostate. This is of very limited efficacy, however, because the posterior rectum is rarely a cause of rectal bleeding. A more common cause of rectal bleeding is damage to the anterior rectum that is directly adjacent to the posterior prostate.

More recent attempts at minimizing rectal bleeding using balloon catheters force the prostate into a fixed position to allow the radiation beam to be more precisely directed to the target tissue. The balloon catheter apparatuses disclosed in the prior art attempt to stabilize the prostate by using large-volume balloons (e.g. 100 cc or more) and, in some cases, have various protrusions that attempt to create a seating area to receive and immobilize the prostatic bulge. Large volume balloons and balloons with bulges distort the rectal mucosa to seat or "cup" the prostate. Large volume balloons also increase patient discomfort.

U.S. Pat. No. 5,476,095 and U.S. Patent Publication No. 2003/028097 both disclose a rectal balloon apparatus having an inner balloon and an outer balloon, and an overall balloon shape that is round with a saddle-shaped bulge on the anterior surface of the balloon. The inner balloon has an anterior section that is covered with an inelastic, adhesive backed cloth material. As the device is inflated, the inner balloon forces the anterior surface of the outer balloon against the prostatic region of the rectum. More specifically, as the balloon is inflated to approximately 60 cc, a saddle-shaped bulge receives the rectal prostatic bulge inferior to the ampulla of the rectum.

U.S. Patent Publication No. 2009/0221899 discloses a rectal balloon apparatus wherein the balloon element has two inflated conditions. The first inflated condition, occurring when approximately 100 cc of fluid are introduced into the balloon, creates a flat surface with a seating area for the prostate to rest. In the second inflated position, a bulbous portion protrudes from the balloon at a position adjacent to the tip of the balloon. This protrusion occurs when at least 140 cc of fluid are introduced into the balloon. The purpose of the bulbous portion is to better isolate the prostate.

Moreover, previously disclosed embodiments of an intracavity balloon catheter are disclosed in U.S. Pat. No. 8,840,542, the entire contents of which are herein incorporated by reference.

The methods and balloon catheter apparatuses in the prior art have not adequately addressed the causes of rectal bleeding. Indeed, between 20-30% of men still experience rectal bleeding during radiation therapy treatments. Moreover, the use of large volume balloons and balloons with bulges that protrude into the anterior rectum to receive the prostatic bulge increase patient discomfort and may, in some cases, aggravate rectal bleeding.

BRIEF SUMMARY OF THE DISCLOSURE

In one embodiment of the disclosure, an intracavity balloon catheter may include a flexible catheter having a proximal catheter portion, a distal catheter portion having a distal tip, and a fluid passageway between the distal tip and the proximal catheter portion. The intracavity balloon catheter may further include a balloon disposed at the distal end of the catheter, the tip of the flexible catheter extending into the balloon, the balloon having an exterior balloon surface comprising a posterior surface and an anterior surface opposed to the posterior surface, the balloon composed of a center section and at least two side sections. The balloon may be inflatable between a deflated condition and an inflated condition by introduction of a fluid into the balloon from the distal tip of the flexible catheter, the exterior balloon surface having a deflated posterior position and a deflated anterior position in the deflated condition, and the exterior balloon surface having an inflated posterior position and an inflated anterior position in the inflated condition.

In a further embodiment of the disclosure, an intracavity balloon catheter may include a flexible catheter having a proximal catheter portion, a distal catheter portion having a distal tip, and a fluid passageway between the distal tip and the proximal catheter portion. The intracavity balloon catheter may further include a balloon disposed at the distal end of the catheter, the tip of the flexible catheter extending into the balloon, the balloon inflatable between a deflated condition and an inflated condition by introduction of a fluid into the balloon from the distal tip of the flexible catheter. The intracavity balloon catheter may also include a positioning ring comprising a first component matable with a second component at a connection point, and a passage along a longitudinal axis of the positioning ring, the passage having a first opening at a first end of the first component and a second opening at a second end of the second component. The flexible catheter may be positionable through the passage, and the positioning ring may be securable to the flexible catheter between the proximal catheter portion and the distal catheter portion.

BRIEF DESCRIPTION OF THE FIGURES

FIG. 7 illustrates a side perspective view of embodiments of a securing device as may be used with embodiments of an intracavity balloon catheter, the embodiments of the securing device illustrated with a catheter tube as may be used with embodiments of an intracavity balloon catheter;

FIG. 8 illustrates a side perspective of cross sectional views of the embodiments of the securing devices and catheter tube of FIG. 7;

FIG. 9 illustrates a side cross sectional view of an embodiment of a securing device for use with embodiments of an intracavity balloon catheter;

FIG. 9A illustrates an enhanced perspective side view of the latching mechanism of the securing device of FIG. 9;

FIG. 10 illustrates an exploded view of the two components of the securing device of FIG. 9;

FIG. 11 illustrates a side cross sectional view of an embodiment of a securing device for use with embodiments of an intracavity balloon catheter;

FIG. 11A illustrates an enhanced view of the latching mechanism of the securing device of FIG. 11;

FIG. 12 illustrates an exploded view of the two components of the securing device of FIG. 11.

DETAILED DESCRIPTION OF THE DISCLOSURE

Figure 1:
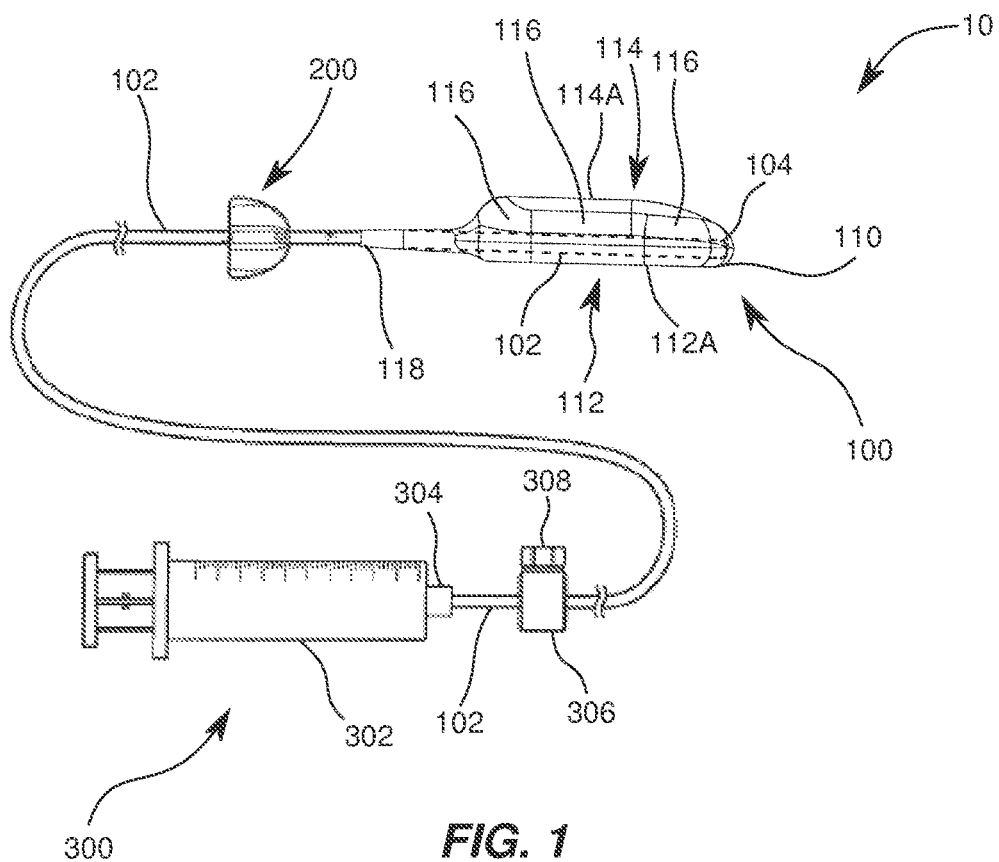
FIG. 1 illustrates a side elevation view of an embodiment of an intracavity balloon catheter in a partially deflated position.

The following detailed description and the appended drawings describe and illustrate some embodiments of the disclosure for the purpose of enabling one of ordinary skill in the relevant art to make and use the embodiments. As such, the detailed description and illustration of these embodiments are purely illustrative in nature and are in no way intended to limit the scope of the disclosure in any manner. It should also be understood that the drawings are not to scale and in certain instances details have been omitted, which are not necessary for an understanding of the disclosure, such as details of fabrication and assembly. In the accompanying drawings, like numerals represent like components.

In one embodiment of the disclosure, an intracavity balloon catheter may include a flexible catheter having a proximal catheter portion, a distal catheter portion having a distal tip, and a fluid passageway between the distal tip and the proximal catheter portion. The intracavity balloon catheter may further include a balloon disposed at the distal end of the catheter, the tip of the flexible catheter extending into the balloon, the balloon having an exterior balloon surface comprising a posterior surface and an anterior surface opposed to the posterior surface, the balloon composed of a center section and at least two side sections. The balloon may be inflatable between a deflated condition and an inflated condition by introduction of a fluid into the balloon from the distal tip of the flexible catheter, the exterior balloon surface having a deflated posterior position and a deflated anterior position in the deflated condition, and the exterior balloon surface having an inflated posterior position and an inflated anterior position in the inflated condition.

In further embodiments of an intracavity balloon catheter, the inflated posterior position and the inflated anterior portion of the center section may be substantially equidistant to the distal catheter portion such that the center section is at least substantially radially symmetric about a longitudinal axis. Each of the side sections may have substantially similar dimensions, and the balloon has a substantially cylindrical shape in the inflated position. The distance between the inflated positions may be greater at the center section than at the side sections. The intracavity balloon catheter may further include a plurality of protrusion provided along at least a portion of the exterior balloon surface, each protrusion having a semi-hemispherical dimension.

In a further embodiment of the disclosure, an intracavity balloon catheter may include a flexible catheter having a proximal catheter portion, a distal catheter portion having a distal tip, and a fluid passageway between the distal tip and the proximal catheter portion. The intracavity balloon catheter may further include a balloon disposed at the distal end of the catheter, the tip of the flexible catheter extending into the balloon, the balloon inflatable between a deflated condition and an inflated condition by introduction of a fluid into the balloon from the distal tip of the flexible catheter. The intracavity balloon catheter may also include a positioning ring comprising a first component matable with a second component at a connection point, and a passage along a longitudinal axis of the positioning ring, the passage having a first opening at a first end of the first component and a second opening at a second end of the second component. The flexible catheter may be positionable through the passage, and the positioning ring may be securable to the flexible catheter between the proximal catheter portion and the distal catheter portion.

In further embodiments of an intracavity balloon catheter may include a plurality of tabs provided proximate to the first end and extending into the passage thereby preventing sliding of an inserted flexible catheter. The plurality of tabs may be resilient and angled towards the passage and the second component. The intracavity balloon catheter may include a plurality of ribs provided proximate to the second end, each rib running parallel to the longitudinal axis of the positioning ring. The intracavity balloon catheter may include a latching mechanism at the connection point, the latching mechanism comprising a first latch on the first component securable with a second latch on the second component. The intracavity balloon catheter may further include a locking mechanism provided about the passage between the first end and the second end, the locking mechanism including a plurality of tabs projecting towards the passage.

Figure 2:
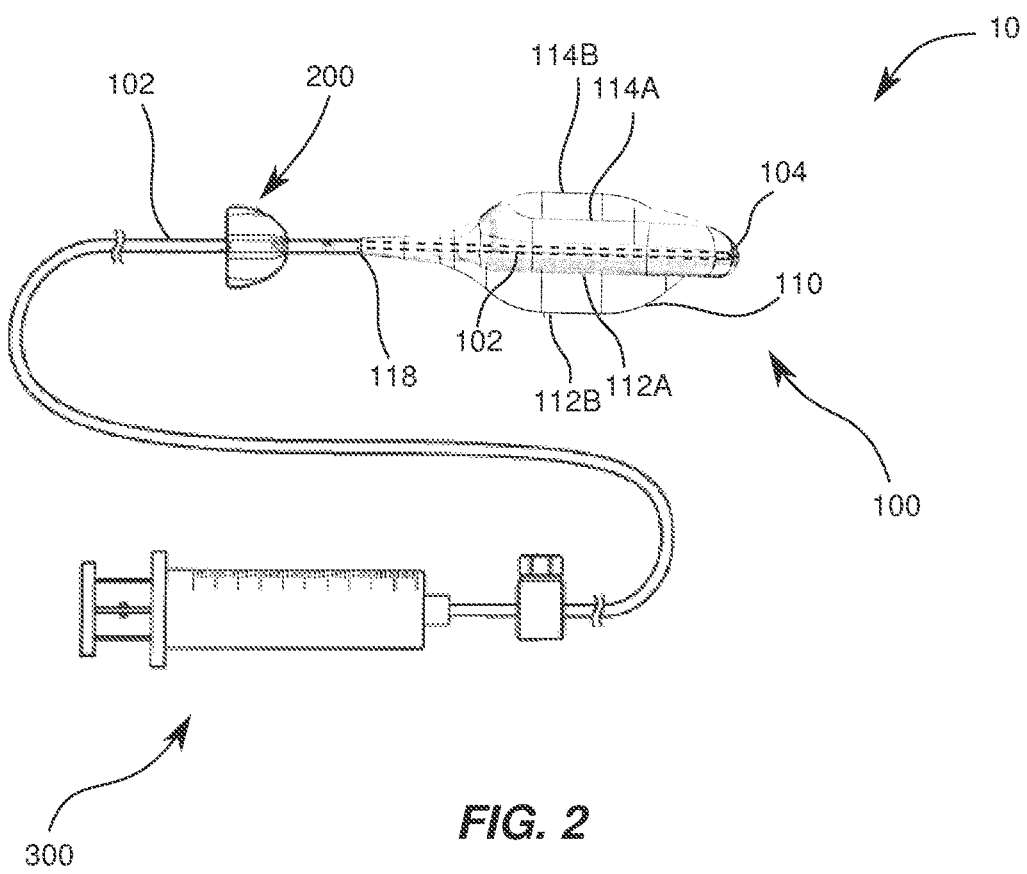
FIG. 2 illustrates a side elevation view of the intracavity balloon catheter of FIG. 1 illustrating the change from a deflated position to an inflated position.
Figures 3, 4:
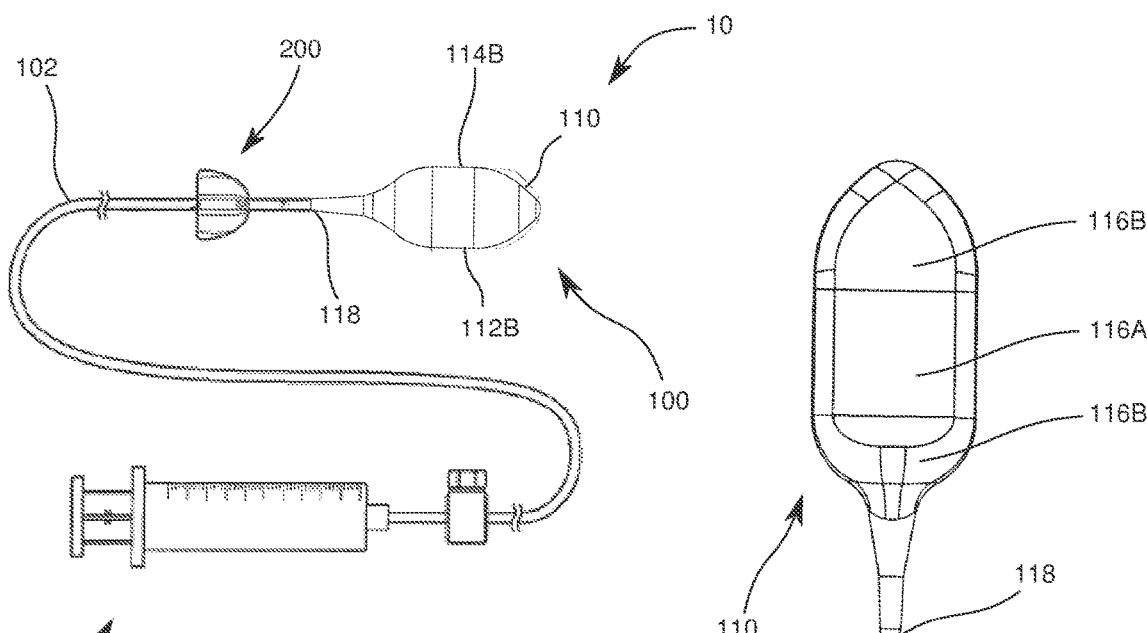
FIG. 3 illustrates a side elevation view of the intracavity balloon catheter of FIG. 1 in an inflated position.
FIG. 4 illustrates a top view of an embodiment of the balloon used with the intracavity balloon catheter of FIG. 1.

FIGS. 1-3 illustrate an embodiment of an intracavity balloon catheter 10 having an inflatable balloon portion 100, a locking device 200, and an inflation device 300. Inflatable balloon portion 100 may include an inflatable balloon 110 and a flexible catheter tube 102 projecting or extending into inflatable balloon 110. Air or another fluid may be injected into balloon 110 through an opening, which in one embodiment is positioned at or proximate to the distal tip 104 of balloon catheter 102. Balloon 110 may have a posterior surface 112 and an anterior surface 114, and may be constructed from a plurality of sections 116. Balloon 110 may be attached to flexible catheter 102 at a joint 118, thereby sealing the interior of balloon 110 from the environment and permitting inflation and deflation upon insertion or removal of fluid through catheter 102.

Balloon 110 may be made from a thin, elastic material such as PVC, polyurethane or a similar material. In some embodiments, anterior surface 114 is reinforced with silicone or another semi-flexible material. The reinforced nature of the anterior surface 114 will result in less elasticity than posterior surface 112. When balloon 110 inflates, posterior surface 112 may expand from a deflated posterior position 112A to an inflated posterior position 112B, and anterior surface 114 may expand from a deflated anterior position 114A to an inflated anterior position 114B. Where anterior portion 114 is constructed from a reinforced material, it will expand a shorter distance than posterior portion 112. Described another way, the distance between the deflated and inflated posterior positions 112A, 112B will be greater than the distance between the deflated and inflated anterior positions 114A, 114B. In embodiments where anterior surface 114 is reinforced, it may be appreciated that balloon 110 will have greater expansion in the direction towards the posterior surface 112, and the restrained expansion of anterior surface 114 may prevent anterior surface 114 forcibly expanding into the anterior tissue of the cavity which balloon 110 is inserted into, thereby reducing pressure or compression of the anterior tissue of the cavity.

In order to provide fluid to inflatable balloon portion 100, an inflation device 300 may be connected to flexible catheter 102 at the end opposite of its distal tip 104. One embodiment of inflation device 300 includes a syringe 302, a port 304, and a valve 306 which may be operated by a switch 308. In one embodiment, valve 306 is a stopcock and switch 308 is an arm handle. Catheter 102 may be joined with syringe 302 at port 304, for instance by a threaded connection. Once joined, syringe 302 may pressurize or depressurize balloon 110 through catheter 102. Valve 306 may operate to prevent unintended inflation or deflation of balloon 110, as well as to maintain a constant pressurization of balloon 110 in order to, for instance, maintaining the inflated state of balloon 110. Switch 308 may be manually operated by a user of intracavity balloon catheter 10 thereby allowing fluids to selectively through catheter 102 into balloon 110. With valve 306 closed or sealed, syringe 302 may be released from catheter 102 as desired by the operator. In one embodiment, balloon 110 may receive between 40 cc and 70 cc of fluid from inflation device 300. It should be understood and appreciated that while most embodiments of syringe 302 are manually operated, other pressurization devices for adding or removing fluid from balloon 110, including automated pumps, are contemplated in alternative embodiments.

Figures 5, 6:
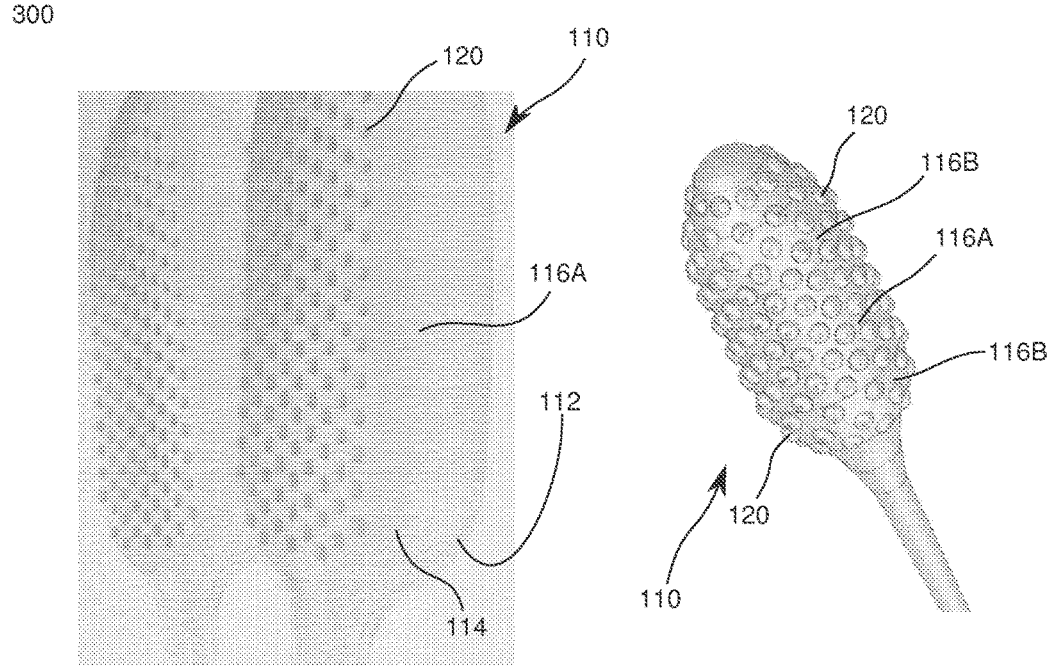
FIG. 5 illustrates a side perspective view of an embodiment of a balloon as may be used with embodiments of an intracavity balloon catheter.
FIG. 6 illustrates a side perspective view of an embodiment of a balloon as may be used with embodiments of an intracavity balloon catheter.

FIGS. 3-5 illustrate embodiments of balloon 110 in an inflated state. As may be appreciated in the illustration, balloon 110 may be manufactured from a plurality of sections 116, including a center section 116A and a plurality of side sections 116B. When inflated, at least center section 116A may inflate to a cylindrical shape having radial symmetry about a longitudinal axis from a cross sectional perspective. Side sections 116B may further inflate, giving inflated balloon 100 an overall substantially cylindrical, quasi-cylindrical, semi-cylindrical or pillow shape, with or without tapered proximal and distal portions. Such a shape may occur by constructing the ends of center section 116A to be approximately parallel from one another. In one embodiment, the diameter of balloon 110 at center section 116A may be about 0.35 inches. Side section 116B may be of varying sizes and dimensions, and in some embodiments side sections 116B on either side of center section 116A may be substantially the same. Protrusions 120 may also be provided on the surface of balloon 110, and in one embodiment protrusions 120 are provided along the anterior surface 114. Protrusions 120 may have a small elevation height, at least compared to the diameter of center section 116A, so as to assist in stabilization of the inserted and inflated balloon 110 while not contributing to excessive compression on an anterior surface. Protrusions 120 may be hemispherically-shaped and may be uniformly distributed across at least a portion of the surface.

FIG. 6 illustrates an additional embodiment of balloon 110. Here, the side sections 116B immediately adjacent to either side of center section 116A are substantially the same, thereby resulting in a substantially, cylindrically shaped inflated balloon 110. Additionally, this embodiment illustrates where protrusions 120 are distributed across both anterior and posterior surfaces 112, 114.

FIGS. 7 and 8 illustrate various embodiments of a locking device 200, each embodiment of which having a through passage 202 which catheter tube 102 is dimensioned to pass through. It should be understood that while three embodiments of locking device 200 (200A, 200B, 200C) are illustrated in these figures, only one locking device 200 is necessary in any given embodiment while three possible embodiments are simultaneously illustrated in these figures for comparison purposes. In use, such as when balloon 110 is properly positioned within a patient, locking device 200 may be axially adjusted along catheter tube 102 and secured against the external sphincter to prevent migration of inserted balloon 110. One locking device embodiment is positioning ring 200A, previously disclosed in U.S. Pat. No. 8,840,542, the contents of which are herein incorporated by reference in its entirety. Positioning ring 200A may include a latch 210 and a receiving slot adjacent latch 210, whereby latch 210 may be snap fittable into the receiving slot, having the effect of squeezing positioning ring 200A about catheter 102. This squeezing prevents positioning ring 200A from sliding along catheter 102. As latch 210 is released, then positioning ring 200A may slide along catheter 102.

With reference now to FIGS. 9 and 10, an embodiment of securing device 200 may be a positioning ring 200B including a first component 220 configured to snap fit or otherwise mate with a second component 222 at a connection point 240. A first end 202A of through passage 202 may be associated with first component 220, while a second end 202B of through passage 202 may be associated with second component 222. A locking mechanism 230 may be provided in order to secure the position of positioning ring 200B. In one embodiment, locking mechanism 230 includes a plurality of tabs 232, which may be resilient or flexible, that project through passage 202 and are angled away from first end 202A. Tabs 232 permit positioning ring 200B to be slid along an inserted catheter tube 102 in the direction towards second end 202B, but simultaneously limit or prevent sliding of positioning ring 200B in the opposite direction towards first end 202A. In order to maintain alignment of catheter tube 102 with through passage 202, a plurality of ribs 234 may be provided on second component 222. These ribs 234 may run parallel to, and along a portion of, through passage 202.

First component 220 may be detachably secured with second component 222 by a latching mechanism 240. In one embodiment, latching mechanism includes a first latch 242 on first component 220 and a second latch 244 on second component 222. Positioning of each latch 242, 244 adjacent to one another may then secure first and second components 220, 222 together. Similarly, first and second components 220, 222 may be detached by rotating one component with respect to another thereby separating latches 242, 244. One embodiment may provide a pair of latching mechanisms 240 provided opposite sides of joined first and second components 220, 222. FIG. 9A further illustrates an embodiment of latching mechanism 240, with the outer shell of components 220, 222 shown transparently.

FIGS. 11 and 12 illustrate an embodiment of securing device 200, which may be a positioning ring 200C. In this embodiment, second component 222 is substantially the same as the second component 222 shown and described in positioning ring 200B, however locking mechanism 230 may be a separate component from first component 220, and may be insertable between first and second components 220, 222. Therefore, positioning ring 200C may be composed of three separable components: first component 220, second component 222, and locking mechanism 230. In one embodiment, locking mechanism 230 includes a plurality of flexible tabs 232, of which may project towards through passage 202 and angled in the direction away from first end 202A. Tabs 232 may permit positioning ring 200C to be slid along an inserted catheter tube 102 in the direction towards second end 202B, but simultaneously prevent sliding of positioning ring 200B in the opposite direction towards first end 202A. Ribs 234 may be provided parallel to passage 202 on first component 220, on second component 222, or on both components.

Figure 13:
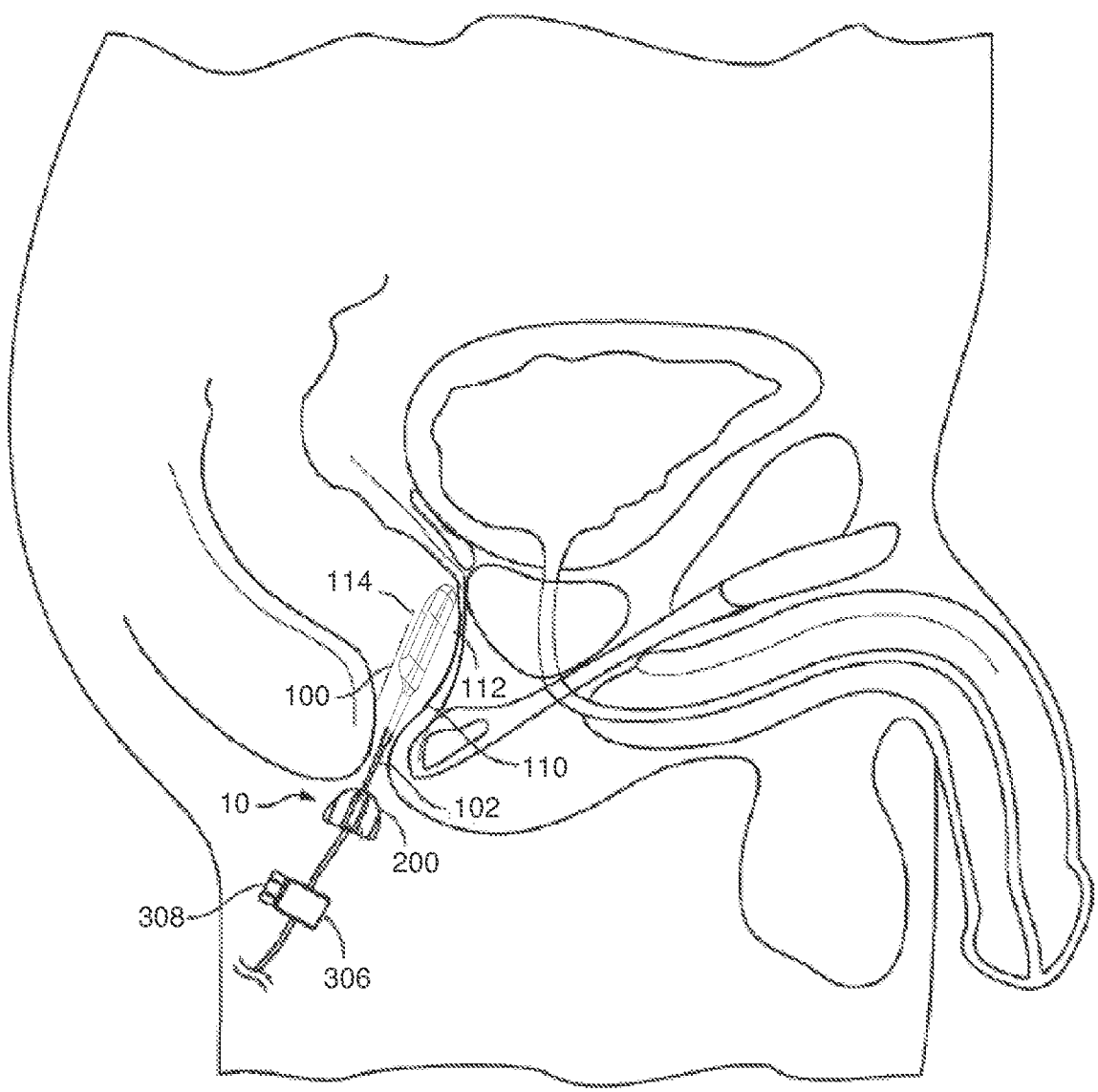
FIG. 13 illustrates a method of using an embodiment of an intracavaity balloon catheter, shown in a deflated condition, for immobilizing the prostate during staging process and radiation therapy treatment.

Referring to FIG. 13, a method of using the intracavity balloon catheter 100 is shown. FIG. 12 shows the intracavity balloon catheter 100 in the anal cavity with the balloon 110 in the inflated position. The desired depth may be attained through use of numerical markings on the catheter 102. The external securing device 200 is placed against the external sphincter and secured to prevent inadvertent movement of the device 100 during use. The planar anterior surface 114 rests against the anterior rectal mucosa and the balloon 110 is expanded upon introduction of fluid. Valve 306, as controlled by switch 308, may operate to maintain a constant pressurization of balloon 110. In addition to the rectal application shown, a method of using intracavity balloon catheter 100 may include insertion of the device 100 in alternative cavity, such as the vagina, esophagus, abdominal cavity, or other parts of the body reachable by an insertable probe.

The balloon can be coated with radioprotective materials to provide further protection to the rectal mucosa against the negative effects of radiation therapy. Exemplary radioprotective elements include Vitamin A, Vitamin E, misoprostal, amifostine, formalin solution and sulfasalazine. The radioprotective material can be chemically bonded to the balloon during the manufacturing process or it can be applied to the balloon prior to insertion.

Alternatively, the balloon can have both a reinforced anterior surface and reinforced posterior surface with less elasticity than the lateral surfaces of the balloon. During inflation, expansion would occur in the lateral directions and both the reinforced anterior surface and the reinforced posterior surface would remain substantially planar, thereby reducing compression of the rectal mucosa in both the anterior and posterior directions. The distal portion of the catheter can be connected to the anterior surface of the lumen of the balloon to restrict rotation between the catheter and the balloon. Exemplary mechanisms of connecting the distal portion of the catheter to the interior anterior surface of the balloon include through mechanical connection, chemical bonding or welding process.

Embodiments of the disclosure may generally relate to intracavity probes, and more specifically intrarectal probes and methods of using the probes for immobilizing the prostate during staging purposes and radiation therapy treatment. Although the probes are described herein as principally to image and immobilize the prostate, it should be understood that the disclosure is equally application to other application necessitating an imaged and immobilized area and for other anatomical regions of interest, such as parts of the body reachable by an insertable probe. Embodiments disclosed herein may aim to improve the reproducibility day to day in the patient by having a substantially cylindrical balloon shape that minimizes the impact of positioning changes. Such a cylindrical shape may thereby remove variations caused by depth being symmetrical along a longitudinal axis. Balloon embodiments may incorporate surface modification of the balloon that create small (essentially not visible through convention imaging) changes in the depth of the rectal mucosa having a radioprotective effect on the rectal mucosa while not affecting the gross relative position of the prostate day to day. The various embodiments of the device disclosed herein may have an application for providing delivery of radioprotective materials to a treatment area in a manner such that surrounding tissue is actively protected from over-exposure to radiation delivery.

The descriptions set forth above are meant to be illustrative and not limiting. Various modifications of the invention, in addition to those described herein, will be apparent to those skilled in the art from the foregoing description. Such modifications are also intended to fall within the scope of the concepts described herein. The disclosures of each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of some implementation should not be construed as an intent to exclude other implementations. For example, artisans will understand how to implement the invention in many other ways, using equivalents and alternatives that do not depart from the scope of the invention. Moreover, unless indicated to the contrary in the preceding description, none of the components described in the implementations are essential to the invention. It is thus intended that the embodiments disclosed in the specification be considered as illustrative, with a true scope and spirit of the invention being indicated by the following claims.

What is claimed:

1. An intracavity balloon catheter comprising: a flexible catheter having a proximal catheter portion and an intermediate catheter portion, and a fluid passageway between the intermediate catheter portion and the proximal catheter portion; and a balloon disposed at the intermediate catheter portion, the balloon having an exterior balloon surface comprising a posterior surface and an anterior surface opposed to the posterior surface, the balloon composed of a center section and at least two side sections, wherein the balloon is inflatable between a deflated condition and an inflated condition by introduction of a fluid into the balloon from the intermediate catheter portion, the exterior balloon surface having a deflated posterior position and a deflated anterior position in the deflated condition, and the exterior balloon surface having an inflated posterior position and an inflated anterior position in the inflated condition, wherein the inflated posterior position and the inflated anterior position of the center section are substantially equidistant to the distal catheter portion such that the center section is at least substantially radially symmetric about a longitudinal axis.

2. The intracavity balloon catheter of claim 1, wherein the balloon has a substantially cylindrical, quasi-cylindrical, semi-cylindrical or pillow shape in the inflated condition.

3. The intracavity balloon catheter of claim 2, wherein the balloon has a substantially cylindrical shape in the inflated condition.

4. The intracavity balloon catheter of claim 1, wherein the distance between the inflated posterior position and the inflated anterior position is greater at the center section than at the side sections.

5. The intracavity balloon catheter of claim 1, further comprising a plurality of protrusions provided along at least a portion of the exterior balloon surface, each protrusion having a semi-hemispherical dimension.

6. The intracavity balloon catheter of claim 1, further comprising a positioning ring comprising a first component matable with a second component at a connection point, and a passage along a longitudinal axis of the positioning ring, the passage having a first opening at a first end of the first component and a second opening at a second end of the second component, wherein the flexible catheter is positionable through the passage, and wherein the positioning ring is securable to the flexible catheter between the proximal catheter portion and the distal catheter portion.

7. The intracavity balloon catheter of claim 6 further comprising a plurality of tabs provided proximate to the first end and extending into the passage thereby preventing sliding of an inserted flexible catheter.

8. The intracavity balloon catheter of claim 7, wherein the plurality of tabs are resilient and angled towards the passage and the second component.

9. The intracavity balloon catheter of claim 6 further comprising a plurality of ribs provided proximate to the second end, each rib running parallel to the longitudinal axis of the positioning ring.

10. The intracavity balloon catheter of claim 6, further comprising a latching mechanism at the connection point, the latching mechanism comprising a first latch on the first component securable with a second latch on the second component.

11. The intracavity balloon catheter of claim 6 further comprising a locking mechanism provided about the passage between the first end and the second end, the locking mechanism including a plurality of tabs projecting towards the passage.

* * * * *